(12) United States Patent
Shields et al.

(10) Patent No.: US 7,888,330 B2
(45) Date of Patent: Feb. 15, 2011

(54) PHOSPHORAMIDATE DERIVATIVES OF FAU

(75) Inventors: Anthony F. Shields, Bloomfield Hills, MI (US); Jiri Zemlicka, Warren, MI (US); Sridhar Nimmagadda, Baltimore, MD (US)

(73) Assignee: Wayne State University, Detroit, MI (US)

( * ) Notice: Subject to any disclaimer, the term of this patent is extended or adjusted under 35 U.S.C. 154(b) by 375 days.

(21) Appl. No.: 12/092,999

(22) PCT Filed: Nov. 9, 2006

(86) PCT No.: PCT/US2006/043882
§ 371 (c)(1),
(2), (4) Date: Jul. 28, 2008

(87) PCT Pub. No.: WO2007/056596
PCT Pub. Date: May 18, 2007

(65) Prior Publication Data
US 2008/0292553 A1 Nov. 27, 2008

Related U.S. Application Data

(60) Provisional application No. 60/734,804, filed on Nov. 9, 2005.

(51) Int. Cl.
*A01N 43/04* (2006.01)
*A61K 31/70* (2006.01)
*A61K 49/04* (2006.01)
*A61K 51/00* (2006.01)
*C07H 19/10* (2006.01)
*C07H 19/048* (2006.01)

(52) U.S. Cl. .................. 514/51; 424/1.73; 424/9.43; 536/26.8

(58) Field of Classification Search .................. None
See application file for complete search history.

(56) References Cited

U.S. PATENT DOCUMENTS

| | | | |
|---|---|---|---|
| 6,677,314 B2 * | 1/2004 | Klecker et al. | 514/44 R |
| 6,677,315 B2 * | 1/2004 | Klecker et al. | 514/44 R |
| 6,682,715 B2 * | 1/2004 | Klecker et al. | 424/1.11 |
| 6,683,601 B2 | 1/2004 | Okamoto | |

FOREIGN PATENT DOCUMENTS

| | | |
|---|---|---|
| WO | WO-9930561 A1 | 6/1999 |
| WO | WO-2007056596 A2 | 5/2007 |
| WO | WO-2007056596 A3 | 5/2007 |

* cited by examiner

*Primary Examiner*—Traviss C McIntosh, III
(74) *Attorney, Agent, or Firm*—Michael Haukaas

(57) ABSTRACT

The present invention provides phosphoramidate derivatives of a furanosyluracil analog, FAU, that can effectively deliver FAU monophosphate, or a derivative thereof, intracellularly. FAU-Phosphoramidate diesters can bypass the first step of phosphorylation and be activated intracellularly so as to be converted to nucleoside monophosphates. This results in improved formation of nucleoside triphosphates, and higher incorporation into DNA. The compounds of the invention can be used to treat cancer.

18 Claims, 5 Drawing Sheets

PHOSPHORAMIDATE DERIVATIVES OF FAU

CROSS-REFERENCE TO RELATED APPLICATIONS

This application is a U.S. National Stage Filing under 35 U.S.C. 371 from International Application Number PCT/US2006/043882, filed Nov. 9, 2006 and published in English as WO 2007/056596 on May 18, 2007, which claims the benefit under 35 U.S.C. 119(e) of U.S. Provisional Application No. 60/734,804, filed on Nov. 9, 2005, which applications and publication are hereby incorporated by reference in their entirety.

GOVERNMENT FUNDING

This invention was made with Government support under NIH Contract No. CA83131A. The United States Government has certain rights in this invention.

BACKGROUND OF THE INVENTION

FAU (1-(2'-deoxy-2'-fluoro-β-D-arabinofuranosyl)-uracil) has been studied as a potential therapeutic and PET imaging agent. The mechanism by which FAU exerts cytotoxicity is not yet well understood but is likely due to either inhibition of DNA or RNA synthesis and/or toxicity once incorporated into DNA. FAU was designed to take advantage of high thymidylate synthase (TS) expression levels observed in breast, colorectal, head and neck cancers that become resistant to 5-fluorouracil (5FU) treatment. Once FAU is taken up into cells, it is phosphorylated to FAU monophosphate (FAUMP) by thymidine kinase (TK) and then methylated by thymidylate synthase to FMAUP (Collins et al., 1999). After further phosphorylation, FMAU-TP is utilized in DNA synthesis (Klecker et al., 1994). So instead of inhibiting TS, an anti-neoplastic drug targeting strategy, FAU is activated by the high TS levels into a cytotoxic drug. See, also U.S. Pat. Nos. 6,682,715; 6,667,314; and 6,703,374.

Studies have demonstrated that [C-14]FAU is incorporated into DNA as 2'-F-ara-5-methyl-deoxyuridine (FMAU), and this appears to be its mode of cytotoxicity (Collins et al., 1999). After incubation of cell lines with FAU or FMAU, the percentage of thymidine replaced correlated with growth inhibition (Collins et al., 1999). These in vitro studies were further supported by in vivo studies in mice showing the incorporation of FAU into DNA as FMAU (Wang et al., 2002). This males FAU a particularly attractive drug, since tumors that are resistant to 5-fluorouracil (5FU) and other TS inhibitors are expected to be more sensitive to FAU toxicity. However, preliminary studies of FAU as an imaging agent demonstrated that it was poorly concentrated in normal proliferating tissues such as marrow in dogs or humans, although modest increased uptake was seen in some tumors (Sun, 2003), potentially limiting its therapeutic effectiveness. In concurrence with this observation, in vitro TK assays showed that FAU is a very poor substrate for mammalian cytologic thymidine kinase (TK1) relative to thymidine or FMAU (Sun et al., 2003). This preliminary data suggests that FAU would be of limited efficacy as an imaging or therapeutic agent since its activation is inhibited at the first phosphorylation step. While there is no evidence that TS activation would not become another hurdle, a recent report (Eiseman et al., 2004) showed that TS activation is the most determinant step for incorporation of FAU into DNA. In principle, administration of 5'-phosphate would aid in overcoming this problem. However, because phosphates are strongly acidic and thus negatively charged at physiological pH, they are too hydrophilic to penetrate the lipid-rich cell membranes. Furthermore, extracellular phosphatases are likely to remove the phosphate. Therefore, there is a need for strategies to circumvent the poor phosphorylation of FAU by mammalian thymidine kinases.

SUMMARY OF THE INVENTION

The present invention provides phosphoramidate derivatives of FAU that can effectively deliver FAU monophosphate intracellularly. The present FAU-Phosphoramidate diesters can bypass the first step of phosphorylation and be activated intracellularly so as to be converted to nucleoside monophosphate. This results in improved formation of nucleoside triphosphate, and higher incorporation into DNA.

Thus, the present invention includes a compound of formula I:

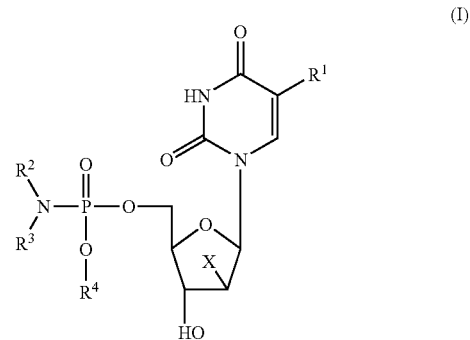

wherein
$R^1$ is H, F, or $(C_1-C_4)$alkyl;
X is halo;
$R^4$ is aryl, heteroaryl, or heterocycle, optionally substituted with 1-3 nitro, 1-5 halo, 1-3 $(C_1-C_6)$alkyl, 1-2 $CF_3$ groups, or a combination thereof;
$R^2$ and $R^3$ are individually H or $(C_1-C_6)$alkyl optionally substituted with 1 or 2 hydroxy, $(C_1-C_6)$alkoxy, $(C_1-C_6)$alkylthio, phenyl, $(C_6-C_{12})$aryloxy, cyano, $(C_1-C_6)$alkoxycarbonyl, amido, $(C_1-C_6)$alkyl-amido, $(C_1-C_6)$alkylsulfonyl, $(C_6-C_{12})$arylsulfonyl, $(C_1-C_6)$perfluoroalkyl-sulfonyl, $(C_1-C_6)$alkylsulfinyl, and $(C_6-C_{12})$arylsulfinyl, or $R^2$ and $R^3$ taken together with N are a 5- or 6-membered heteroaryl or heterocyclic ring optionally containing 1 or 2 additional S, N, or O atoms, wherein N is substituted with $R^5$ and $R^5$ is H, O, $(C_1-C_4)$alkyl, phenyl, or benzyl;
with the proviso that one of $R^2$ and $R^3$ is not H;
or a pharmaceutically acceptable salt thereof.

In one embodiment of the invention, $R^1$ is H or methyl.
In one embodiment of the invention, X is F, Cl, Br, or I. In one specific embodiment, X is F.
In one embodiment of the invention, $R^4$ is phenyl.
In another embodiment of the invention, $R^2$ is H.
In another embodiment of the invention, $R^3$ is phenyl$(C_1-C_4)$alkyl. In various embodiments, the $(C_1-C_6)$alkyl of $R^2$ and $R^3$, when present, are substituted with one of more (e.g., 1 to 8, 1 to 5, 1 to 3, or 1 to 2) of the recited substituents.
In various embodiment of the invention, $(R^2)(R^3)N—$ is the residue of an α-amino acid, such as a naturally occurring amino acid, or all amide or $(C_1-C_4)$alkylamide thereof.
For example, $R^3$ can be $(C_1-C_4)$alkoxycarbonyl$(C_1-C_6)$alkyl, such as 1-(($C_1-C_4)$alkoxycarbonyl)ethyl.

Some of the compounds of formula I are useful as intermediates to prepare other compounds of formula I.

A preferred compound of formula I has the structure:

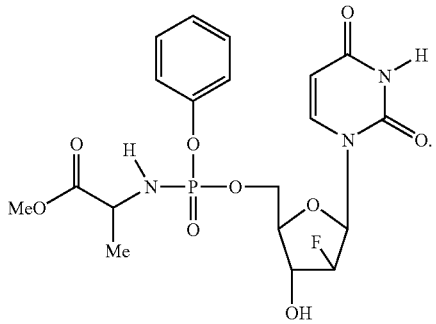

The invention also provides a pharmaceutical composition, such as a unit dosage form, comprising a compound of formula I, or a pharmaceutically acceptable salt thereof, in combination with a pharmaceutically acceptable diluent or carrier, and can optionally include stabilizers, preservatives, buffers, and absorption control agents.

The present invention also includes a method of inhibiting the growth of a cancer cell by contacting a population of said cells with an effective growth inhibiting amount of a compound of formula I. The method of inhibiting the growth of a cancer cell can be in vivo or in vitro. The method of inhibition includes administering the compound of formula I to a mammal, such as a human, afflicted with cancer.

The invention further provides the use of the compounds disclosed herein for medical therapy. Also provided is the use of one or more of the compounds disclosed herein to prepare a medicament for treating cancer.

The compound of formula I is particularly effective to treat cancers susceptible to 5-FU, such as breast, colorectal, head or neck cancer.

The compound of formula I can be administered parenterally, or orally.

The present invention also includes a method of imaging a tumor comprising administering to a mammal afflicted with a tumor, an effective imaging amount of a compound of formula I comprising a radionuclide, and employing the techniques of positron emission tomography (PET) to produce images of said tumor.

In a preferred embodiment of the invention, X is a radionuclide, e.g., X is $^{18}$F.

BRIEF DESCRIPTION OF THE FIGURES

FIG. 2 represents the intracellular accumulation of FAU-PA and FAU. FIG. 3 shows the acid extraction analysis results. Cells were incubated with 1 μCi/mL of either FAUPA or FAU for 2 hours. At the end of the incubation, cells were rinsed, trypsinized and the cell pellets were lysed with PCA or whole pellets were dissolved in soluene-350. All the fractions were mixed with ultima gold and counted for 5 minutes.

DETAILED DESCRIPTION OF THE INVENTION

Many current antiviral and anticancer therapies are targeted to inhibit DNA synthesis, making the role of nucleosides and nucleotides in therapeutic drug development more prominent. For a nucleoside to be incorporated into DNA, it must be first phosphorylated by nucleoside kinases to the corresponding mono, di and triphosphate. Therapies that involve long-term administration of nucleosides such as 5FU and AZT tend to develop resistance due to decreased activity of cytosolic thymidine kinase (Wu et al., 1995; Antonelli et al. 1996; Turriziani et al., 1996; Inaba et al., 1998). This has prompted the development of prodrugs that could intracellularly deliver the nucleotides. These prodrugs could circumvent the dependence on endogenous thymidine kinase. Nucleoside prodrugs are well studied as antiviral agents for HIV, CMV and other viral infections (Farrow et al., 1990; Valette et al., 1996; Winter et al., 1996; Balzarini et al., 1997). One such class of molecule is phosphoramidate diester (Zemlicka, 2002).

Figure 1:
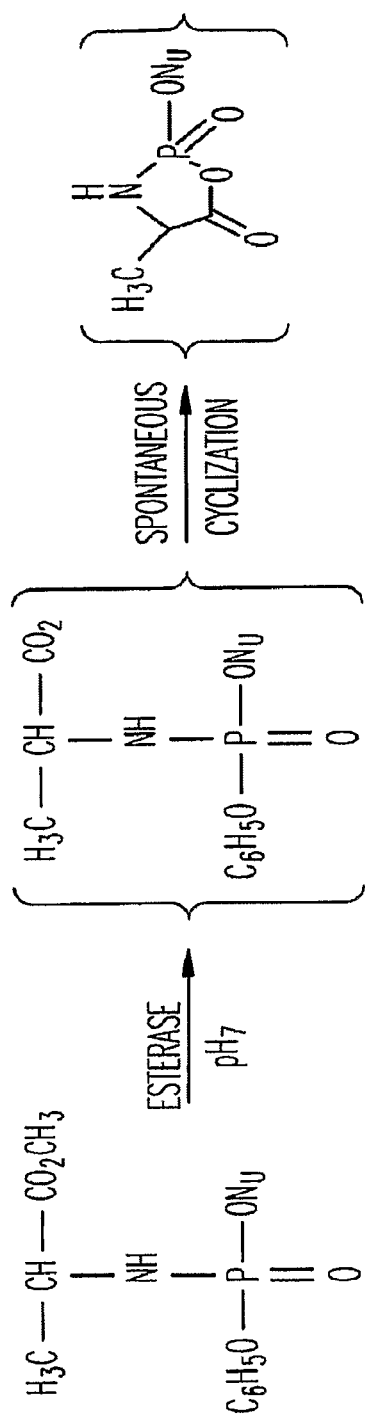
FIG. 1 is a reaction scheme depicting phosphoramidate activation. Once inside the cell, phosphoramidates are initially cleaved by esterases. The resulting intermediate undergoes spontaneous cyclization and chemical hydrolysis to give an amino acyl metabolite (AAM). The P—N bond in AAM is further cleaved by phosphoramidases resulting in a nucleoside phosphate. Nu: nucleoside.
Figure 1:
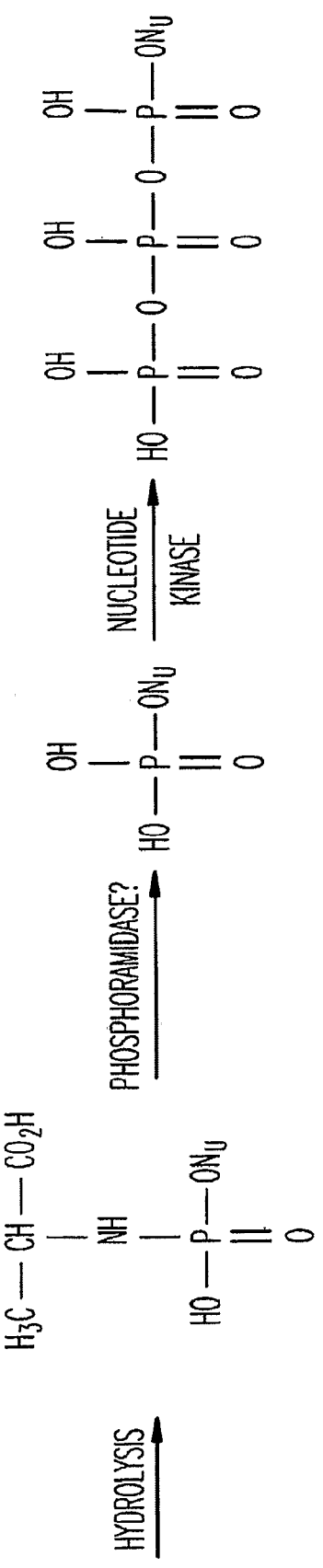

As shown in FIG. 1, the activation of phosphoramidate diesters consists of the following steps:

a. carboxyl esterase mediated hydrolysis of the carboxylic ester function in the amino acid ester moiety (McGuigan et al., 1998a; McGuigan et al., 1998b);

b. intramolecular nucleophilic attack of phosphorus by the carboxyl group with spontaneous elimination of phenol after transient formation of a five-membered cyclic intermediate;

c. conversion of dNMP (deoxy nucleoside monophosphate) amino acyl metabolite to free dNMP; and d. cleavage of the P—N bond, predominantly catalyzed by one or more less-specific phosphatases or by a distinct and specific phosphoramidase (Holzer et al., 1962; Holzer et al., 1966; Fernley, 1971; Snyder and Wilson, 1972; Kelly et al., 1975; Nishino et al., 1994).

Phosphoramidases that catalyze the hydrolysis of phosphoramidate compounds have been described in mammalian cells and bacteria (Singer and Fruton, 1957; Stevens-Clark et al., 1968a; Stevens-Clark et al., 1968b; Parvin and Smith, 1969; Kuba et al., 1994; Abraham et al., 1996) and have been characterized in more detail by Shabarova and coworkers (Shabarova and Prokofiev, 1970; Dudkin et al., 1971; McIntee et al., 1997).

Many phosphoramidate prodrugs have been developed including those of AZT (Saboulard et al., 1999), d4T (Balzarini et al., 1996), allene (Winter et al., 1996), 5-FU (R. F. Borch et al., U.S. Pat. No. 5,233,031), cyclophosphamide (R. F. Borch et al., U.S. Pat. No. 5,472,956), and methylenecyclopropane analogs (Qiu et al., 1999) with various combinations of amino acids and carboxylesters. Some of them proved to be intracellularly active and some of them are not, due to poor intracellular conversion.

Compounds of Formula I can be prepared in a one-step process, as taught by Y.-L. Qiu et al. (1999). A compound of formula II can be converted directly to a compound of formula Ia, by reaction with methyl chlorophenylphosphophoryl P→N(H)(R$^2$)(R$^3$), as shown in Scheme 1 using the reagent (III): R—C(H)(CO$_2$Alk)-NHP(O)(Cl)(OR$^4$), wherein R is (C$_1$-C$_6$)alkyl and R$^4$ is phenyl or substituted phenyl.

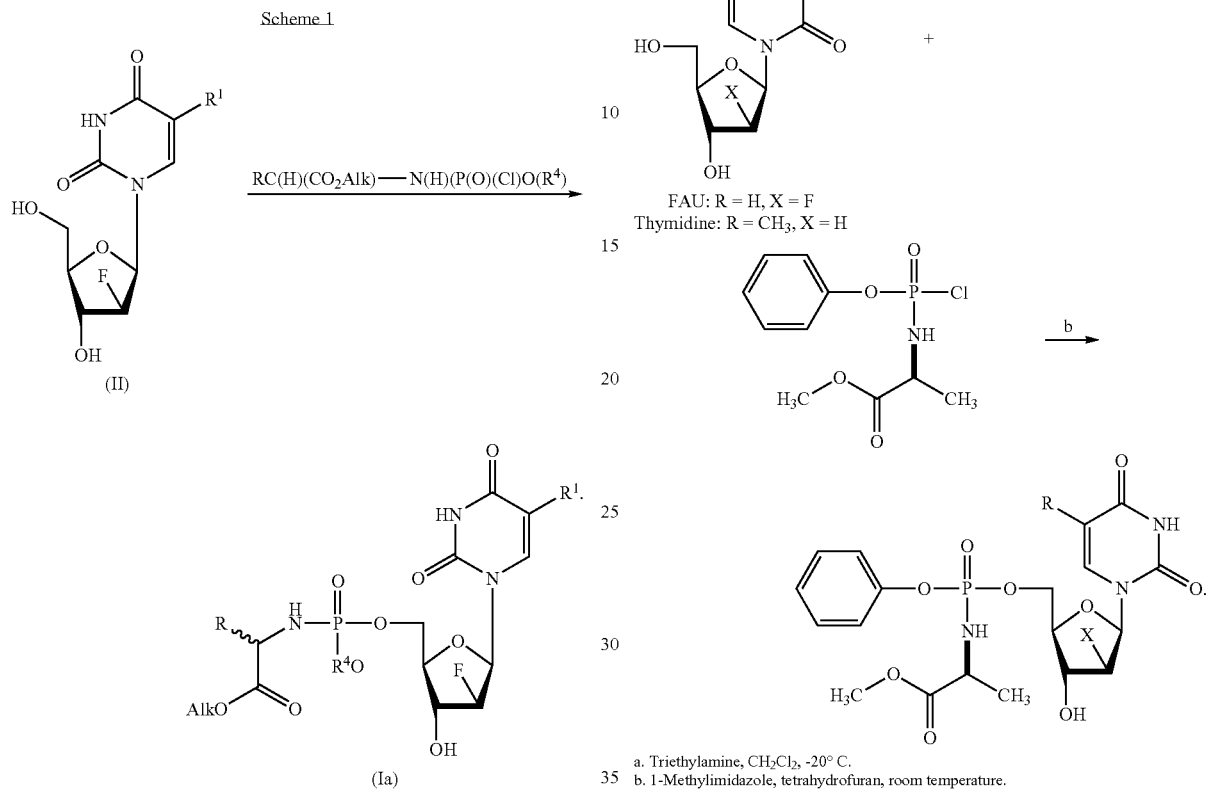

Reagents of general formula (R$^2$)(R$^3$)NP(O)(Cl)(OR$^4$) wherein R$^2$ and R$^3$ are as defined hereinabove can be readily prepared as shown in Scheme 2, wherein R$^2$ is H and R$^3$ is CH(CH$_3$)CO$_2$CH$_3$, by reacting amino acid esters with phenyldichlorophosphate in the presence of an amine base.

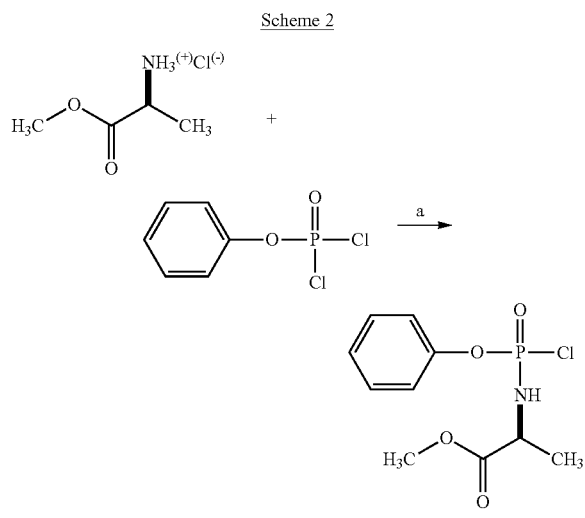

The following definitions are used, unless otherwise described: halo is fluoro, chloro, bromo, or iodo. Alkyl and alkoxy (Alk or AlkO) denote both straight and branched alkyl groups; but reference to an individual radical such as "propyl" embraces only the straight chain radical, a branched chain isomer such as "isopropyl" being specifically referred to. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, (C$_1$-C$_4$)alkyl, phenyl or benzyl, as well as a radical of an ortho-fused bicyclic heterocycle of about eight to ten ring atoms derived therefrom, particularly a benz-derivative or one derived by fusing a propylene, trimethylene, tetramethylene diradical thereto.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or diastereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase) and how to determine anti-infectious activity using the standard tests described herein, or using other similar tests which are well known in the art.

Specific and preferred values listed below for radicals, substituents, and ranges, are for illustration only; they do not exclude other defined values or other values within defined ranges for the radicals and substituents. In various embodiments, a recited substituent can be optionally substituted with 1-3 other substituents, for example, the groups described below.

Specifically, $(C_1-C_6)$alkyl can be methyl, ethyl, propyl, isopropyl, butyl, iso-butyl, sec-butyl, e.g., $(C_1-C_4)$alkyl, or can include pentyl, 3-pentyl, or hexyl; and includes $(C_3-C_6)$cycloalkyl which can be cyclopropyl, cyclobutyl, cyclopentyl, or cyclohexyl, and $(C_3-C_6)$cycloalkyl$(C_1-C_6)$alkyl which can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl.

Aryl refers to an aromatic hydrocarbon group derived from the removal of one hydrogen atom from a single carbon atom of a parent aromatic ling system. The radical can be at a saturated or unsaturated carbon atom of the parent ring system. The aryl group can have from 6 to 18 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or optionally substituted with one or more (e.g., 1 to 5, 1 to 3, or 1 to 2) substituents, for example, the various substituents described herein.

Heterocyclic ring includes the foregoing cycloalkyl wherein the ring optionally comprises 1-2 S, non-peroxide O or N(R) as well as 2-5 carbon atoms; such as morpholinyl, piperidinyl, piperazinyl, pyranyl, tetrahydrofuranyl, indanyl, 1,3-dithian-2-yl, and the like; $(C_1-C_6)$alkoxy (AlkO) can be methoxy, ethoxy, propoxy, isopropoxy, butoxy, iso-butoxy, sec-butoxy, pentoxy, 3-pentoxy, or hexyloxy as well as $(C_3-C_6)$cycloalkyl; $(C_1-C_6)$alkanoyl can be formyl, acetyl, propanoyl or butanoyl; halo$(C_1-C_6)$alkyl can be iodomethyl, bromomethyl, chloromethyl, fluoromethyl, trifluoromethyl, 2-chloroethyl, 2-fluoroethyl, 2,2,2-trifluoroethyl, or pentafluoroethyl; hydroxy$(C_1-C_6)$alkyl can be alkyl substituted with 1 or 2 OH groups, such as hydroxymethyl, 1-hydroxyethyl, 2-hydroxyethyl, 1-hydroxypropyl, 2-hydroxypropyl, 3-hydroxypropyl, 1-hydroxybutyl, 4-hydroxybutyl, 3,4-dihydroxybutyl, 1-hydroxypentyl, 5-hydroxypentyl, 1-hydroxyhexyl, or 6-hydroxyhexyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy. The heterocyclic ring can be unsubstituted or optionally substituted with one or more (e.g., 1 to 5, 1 to 3, or 1 to 2) substituents, for example, the various substituents described herein.

Heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), 1H-indolyl, isoquinolyl (or its N-oxide) or quinolyl (or its N-oxide). The heteroaryl can be unsubstituted or optionally substituted with one or more (e.g., 1 to 5, 1 to 3, or 1 to 2) substituents, for example, the various substituents described herein.

The term "amino acid," includes a residue of a natural amino acid (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl, benzyl, or benzyloxycarbonyl), as well as natural and unnatural amino acids protected at the carboxy or amino terminus (e.g. as a $(C_1-C_6)$alkyl, phenyl or benzyl ester or amide; or as an α-methylbenzyl amide). Other suitable amino and carboxy protecting groups are known to those skilled in the art (See for example, Greene, T. W.; Wutz, P. G. M. *Protecting Groups In Organic Synthesis*, $2^{nd}$ edition, John Wiley & Sons, Inc., New York (1991) and references cited therein).

Generally, both natural and unnatural amino acids and their alkyl esters are useful in the present invention. Many suitable amino acids are commercially available from vendors such as Sigma-Aldrich and Bachem. Specific useful examples of natural amino acids are tryptophan and histidine. Other specific examples include unnatural amino acids, such as 3-(indan-3-yl)-2-aminopropanoic acid, 3-(morpholin-1-yl)-2-aminopropanoic acid, 3-(piperidin-1-yl)-2-aminopropanoic acid, 3-(piperazin-1-yl)-2-aminopropanoic acid, 3-(pyridin-2-yl)-2-aminopropanoic acid, 4-(pyridin-2-yl)-2-aminobutanoic acid, 4-(imidazol-2-yl)-2-aminobutanoic acid, 4-(benzofuran-2-yl)-2-aminobutanoic acid; 3-(1,3-dithian-2-yl)-2-aminopropanoic acid, and the like.

A compound of the present invention also includes a pharmaceutically-acceptable salt, an enantiomer, an isomer, a tautomer, a polymorph, a prodrug, or a derivative thereof. Such salts, for example, can be formed between a positively charged substituent in a compound (e.g., amino) and an anion. Suitable anions include, but are not limited to, chloride, bromide, iodide, sulfate, nitrate, phosphate, citrate, methanesulfonate, trifluoroacetate, and acetate. Likewise, a negatively charged substituent in a compound (e.g., carboxylate) can form a salt with a cation. Pharmaceutically acceptable cations include metallic ions and organic ions. More preferred metallic ions include, but are not limited to appropriate alkali metal (Group Ia) salts, alkaline earth metal (Group IIa) salts and other physiological acceptable metal ions. Exemplary ions include aluminum, calcium, lithium, magnesium, potassium, sodium and zinc in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine.

Exemplary pharmaceutically acceptable acids include without limitation hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalacetic acid, fumaric acid, propionic acid, aspartic acid, glutamic acid, benzoic acid, and the like. Examples of prodrugs include esters and other pharmaceutically acceptable derivatives, which, upon administration to a subject, are capable of providing compounds described above.

The compounds of the present invention are usually administered in the form of pharmaceutical compositions. These compositions can be administered by any appropriate route including, but not limited to, oral, nasogastric, rectal, transdermal, parenteral (for example, subcutaneous, intramuscular, intravenous, intramedullary and intradermal injections, or infusion techniques administration), intranasal, transmucosal, implantation, vaginal, topical, buccal, and sublingual. Such preparations may routinely contain buffering agents, preservatives, penetration enhancers, compatible carriers and other therapeutic or non-therapeutic ingredients.

The present invention also includes a pharmaceutical composition that contains the compound of the present invention associated with pharmaceutically acceptable carriers or excipients. In making the compositions of the present invention, the compositions(s) can be mixed with a pharmaceutically acceptable excipient, diluted by the excipient or enclosed within such a carrier, which can be in the form of a capsule, sachet, or other container. The carrier materials that can be employed in making the composition of the present invention are any of those commonly used excipients in pharmaceutics and should be selected on the basis of compatibility with the active drug and the release profile properties of the desired dosage form.

Illustratively, pharmaceutical excipients are chosen below as examples:

(a) Binders such as acacia, alginic acid and salts thereof, cellulose derivatives, methylcellulose, hydroxyethyl cellulose, hydroxypropyl cellulose, magnesium aluminum silicate, polyethylene glycol, gums, polysaccharide acids, bentonites, hydroxypropyl methylcellulose, gelatin, polyvinylpyrrolidone, polyvinylpyrrolidone/vinyl acetate copolymer, crospovidone, povidone, polymethacrylates, hydroxypropylmethylcellulose, hydroxypropylcellulose, starch, pregelatinized starch, ethylcellulose, tragacanth, dextrin, microcrystalline cellulose, sucrose, or glucose, and the like.

(b) Disintegration agents such as starches, pregelatinized corn starch, pregelatinized starch, celluloses, cross-linked carboxymethylcellulose, sodium starch glycolate, crospovidone, cross-linked polyvinylpyrrolidone, croscarmellose sodium, microcrystalline cellulose, a calcium, a sodium alginate complex, clays, alginates, gums, or sodium starch glycolate, and any disintegration agents used in tablet preparations.

(c) Filling agents such as lactose, calcium carbonate, calcium phosphate, dibasic calcium phosphate, calcium sulfate, microcrystalline cellulose, cellulose powder, dextrose, dextrates, dextran, starches, pregelatinized starch, sucrose, xylitol, lactitol, mannitol, sorbitol, sodium chloride, polyethylene glycol, and the like.

(d) Surfactants such as sodium lauryl sulfate, sorbitan monooleate, polyoxyethylene sorbitan monooleate, polysorbates, polaxomers, bile salts, Pluronic™ line (BASF), oleic acid, glyceryl monostearate, sorbitan monolaurate, triethanolamine oleate, polyoxyethylene sorbitan monolaurate, sodium oleate, and the like.

(e) Stabilizers such as any antioxidation agents, buffers, or acids, and the like, can also be utilized.

(f) Lubricants such as magnesium stearate, calcium hydroxide, talc, sodium stearyl fumarate, hydrogenated vegetable oil, stearic acid, glyceryl behapate, magnesium, calcium and sodium stearates, stearic acid, talc, waxes, Stearowet, boric acid, sodium benzoate, sodium acetate, sodium chloride, DL-leucine, polyethylene glycols, sodium oleate, or sodium lauryl sulfate, and the like.

(g) Diluents such lactose, starch, mannitol, sorbitol, dextrose, microcrystalline cellulose, dibasic calcium phosphate, sucrose-based diluents, confectioner's sugar, monobasic calcium sulfate monohydrate, calcium sulfate dihydrate, calcium lactate trihydrate, dextrates, inositol, hydrolyzed cereal solids, amylose, powdered cellulose, calcium carbonate, glycine, or bentonite, and the like.

(h) Anti-adherents or glidants such as talc, corn starch, DL-leucine, sodium lauryl sulfate, and magnesium, calcium, or sodium stearates, and the like.

(i) Pharmaceutically compatible carrier comprises acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, or pregelatinized starch, and the like.

Additionally, drug formulations are discussed in, for example, Remington's The Science and Practice of Pharmacy (2000). Another discussion of drug formulations can be found in Liberman, H. A. and Lachman, L., Eds., *Pharmaceutical Dosage Forms*, Marcel Decker, New York, N.Y., 1980.

The terms "treat" and "treating" include preventing a pathologic condition from occurring (e.g. prophylaxis); inhibiting the pathologic condition or arresting its development; relieving a subject of the pathologic condition; and/or diminishing symptoms associated with the pathologic condition. "Treat," "treating" or "treatment" includes treating, reversing, preventing, ameliorating, or inhibiting an injury or disease-related condition or a symptom of an injury or disease-related condition.

The term "therapeutically effective amount" or "effective amounts" is intended to include an amount of a compound described herein, or an amount of a compound described herein in combination with another treatment agent, e.g., to treat or prevent a disease or disorder, or to treat the symptoms of a disease or disorder, typically in a host. The combination of compounds can be a synergistic combination. Synergy, as described for example by Chou and Talalay (*Adv. Enzyme Regul.*, 1984, 22, 27), occurs when the effect of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased activity, or some other beneficial effect of the combination compared with the individual components.

A "subject" can be a vertebrate, preferably a mammal, more preferably a human. Mammals include, but are not limited to, humans, farm animals, sport animals, and companion animals.

The compound of formula I is particularly effective to treat cancers susceptible to 5-FU, such as breast, colorectal, head or neck cancer. Breast cancer includes ductal carcinoma in situ (DCIS), lobular carcinoma in situ (LCIS), invasive ductal carcinoma, invasive lobular carcinoma, inflammatory breast cancer, and Paget's disease. Colorectal cancer, also called colon cancer or bowel cancer, includes cancerous growths in the colon, rectum and appendix. Head and neck cancers are malignant growths originating in the lip and oral cavity (mouth), nasal cavity, pharynx, larynx, thyroid, paranasal sinuses, salivary glands and/or cervical lymph nodes of the neck. Head and neck cancers are most commonly squamous cell carcinomas, originating from the squamous cells that line the upper aerodigestive tract. Nasopharyngeal cancer is one specific example of a head and neck squamous cell carcinoma.

For treatment of cancer or other neoplasm, compositions of the invention can be used to provide a dose of a compound of the present invention of about 5 ng to about 1000 mg, or about 100 ng to about 600 mg, or about 1 mg to about 500 mg, or about 20 mg to about 400 mg. Typically a dosage effective amount will range from about 0.0001 mg/kg to 1500 mg/kg, more preferably 1 to 1000 mg/kg, more preferably from about 1 to 150 mg/kg of body weight, and most preferably about 50 to 100 mg/kg of body weight. A dose can be administered in one to about four doses per day, or in as many doses per day to elicit a therapeutic effect. Illustratively, a dosage unit of a composition of the present invention can typically contain, for example, about 5 ng, 50 ng 100 ng, 500 ng, 1 mg, 10 mg, 20 mg, 40 mg, 80 mg, 100 mg, 125 mg, 150 mg, 200 mg, 250 mg, 300 mg, 350 mg, 400 mg, 450 mg, 500 mg, 550 mg, 600 mg, 700 mg, 800 mg, 900 mg, or 1000 mg of a compound of the present invention. The dosage form can be selected to accommodate the desired frequency of administration used to achieve the specified dosage.

In one embodiment of the present invention, the composition is administered to a subject in an effective amount, that is, the composition is administered in an amount that achieves a therapeutically effective dose of a compound of the present invention in the blood serum of a subject for a period of time to elicit a desired therapeutic effect. Illustratively, in a fasting adult human (fasting for generally at least 10 hours) the composition is administered to achieve a therapeutically effective dose of a compound of the present invention in the blood serum of a subject from about 5 minutes after administration of the composition.

In another embodiment of the present invention, a therapeutically effective dose of the compound is achieved in the blood serum of a subject at about 10 minutes from the time of administration of the composition to the subject. In another embodiment of the present invention, a therapeutically effective dose of the compound is achieved in the blood serum of a subject at about 20 minutes from the time of administration of the composition to the subject. In yet another embodiment of the present invention, a therapeutically effective dose of the compound is achieved in the blood serum of a subject at about 30 minutes from the time of administration of the composition to the subject. In still another embodiment of the present invention, a therapeutically effective dose of the compound is achieved in the blood serum of a subject at about 40 minutes from the time of administration of the composition to the subject.

In one embodiment of the present invention, a therapeutically effective dose of the compound is achieved in the blood serum of a subject at about 20 minutes to about 12 hours from the time of administration of the composition to the subject. In another embodiment of the present invention, a therapeutically effective dose of the compound is achieved in the blood serum of a subject at about 20 minutes to about 6 hours from the time of administration of the composition to the subject. In yet another embodiment of the present invention, a therapeutically effective dose of the compound is achieved in the blood serum of a subject at about 20 minutes to about 2 hours from the time of administration of the composition to the subject. In still another embodiment of the present invention, a therapeutically effective dose of the compound is achieved in the blood serum of a subject at about 40 minutes to about 2 hours from the time of administration of the composition to the subject. And in yet another embodiment of the present invention, a therapeutically effective dose of the compound is achieved in the blood serum of a subject at about 40 minutes to about 1 hour from the time of administration of the composition to the subject.

In one embodiment of the present invention, a composition of the present invention is administered at a dose suitable to provide a blood serum concentration with a half maximum dose of a compound of the present invention. Illustratively, a blood serum concentration of about 0.01 to about 1000 nM, or about 0.1 to about 750 nM, or about 1 to about 500 nM, or about 20 to about 1000 nM, or about 100 to about 500 nM, or about 200 to about 400 nM is achieved in a subject after administration of a composition of the present invention.

Contemplated compositions of the present invention provide a therapeutic effect over an interval of about 5 minutes to about 24 hours after administration, enabling once-a-day or twice-a-day administration if desired. In one embodiment of the present invention, the composition is administered at a dose suitable to provide an average blood serum concentration with a half maximum dose of a compound of the present invention of at least about 1 mg/ml, or at least about 5 mg/ml, or at least about 10 mg/ml, or at least about 50 mg/ml, or at least about 100 mg/ml, or at least about 500 mg/ml, or at least about 1000 mg/ml in a subject about 10, 20, 30, or 40 minutes after administration of the composition to the subject.

The amount of the compound of the present invention necessary to elicit a therapeutic effect can be experimentally determined based on, for example, the absorption rate of the compound into the blood serum, the bioavailability of the compound, and the potency for treating the disorder. It is understood, however, that specific dose levels of the compounds of the present invention for any particular subject depends upon a variety of factors including the activity of the specific compound employed, the age, body weight, general health, sex, and diet of the subject (including, for example, whether the subject is in a fasting or fed state), the time of administration, the rate of excretion, the drug combination, and the severity of the particular disorder being treated and form of administration.

Treatment dosages generally may be titrated to optimize safety and efficacy. Typically, dosage-effect relationships from in vitro and/or in vivo tests initially can provide useful guidance on the proper doses for subject administration. Studies in animal models generally may be used for guidance regarding effective dosages for treatment of cancer and other neoplasms in accordance with the present invention. The interrelationship of dosages for animals and humans (based on milligrams per square meter of body surface) is described by Freireich et al., *Cancer Chemother. Rep.* 1966, 50, 219. Body surface area may be approximately determined from height and weight of the patient. See, e.g., Scientific Tables, Geigy Pharmaceuticals, Ardley, N.Y., 1970, 537. Effective doses will also vary, as recognized by those skilled in the art, depending on the route of administration, the excipient usage, and the optional co-administration with other therapeutic agents.

Toxicity and therapeutic efficacy of the active ingredients can be determined by standard pharmaceutical procedures, e.g., for determining $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Generally speaking, one will desire to administer an amount of the compound of the present invention that is effective to achieve a serum level commensurate with the concentrations found to be effective in vitro for a period of time effective to elicit a therapeutic effect. Thus, where a compound is found to demonstrate in vitro activity at, for example, a half-maximum effective dose of 200 nM, one will desire to administer an amount of the drug that is effective to provide about a half-maximum effective dose of 200 nM concentration in vitro for a period of time that elicits a desired therapeutic effect, for example, treating a cancer and other indicators as are selected as appropriate measures by those skilled in the art. Determination of these parameters is well within the skill of the art. These considerations are well known in the art and are described in standard textbooks.

Besides being useful for human treatment, the present invention is also useful for other subjects including veterinary animals, reptiles, birds, exotic animals and farm animals, including mammals, rodents, and the like. Mammal includes a primate, for example, a human, a monkey, or a lemur, a horse, a dog, a pig, or a cat. A rodent includes a rat, a mouse, a squirrel, or a guinea pig.

For oral administration, the pharmaceutical composition can contain a desired amount of a compound of the present invention, and be in the form of, for example, a tablet, a hard or soft capsule, a lozenge, a cachet, a troche, a dispensable powder, granules, a suspension, an elixir, a liquid, or any other form reasonably adapted for oral administration. Illustratively, such a pharmaceutical composition can be made in the form of a discrete dosage unit containing a predetermined amount of the compound such as a tablet or a capsule. Such oral dosage forms can further comprise, for example, buffering agents. Tablets, pills and the like additionally can be prepared with enteric coatings.

Pharmaceutical compositions suitable for buccal or sublingual administration include, for example, lozenges comprising the compound of the present invention in a flavored base, such as sucrose, and acacia or tragacanth, and pastilles comprising the compound in an inert base such as gelatin and glycerin or sucrose and acacia.

Liquid dosage forms for oral administration can include pharmaceutically acceptable emulsions, solutions, suspensions, syrups, and elixirs containing inert diluents commonly used in the art, such as water. Such compositions can also comprise, for example, wetting agents, emulsifying and suspending agents, and sweetening, flavoring, and perfuming agents.

Examples of suitable liquid dosage forms include, but are not limited to, aqueous solutions comprising the compound of the present invention and beta-cyclodextrin or a water soluble derivative of beta-cyclodextrin such as sulfobutyl ether beta-cyclodextrin; heptakis-2,6-di-O-methyl-beta-cyclodextrin; hydroxypropyl-beta-cyclodextrin; and dimethyl-beta-cyclodextrin.

The pharmaceutical compositions of the present invention can also be administered by injection (intravenous, intramuscular, subcutaneous). Such injectable compositions can employ, for example, saline, dextrose, or water as a suitable carrier material. The pH value of the composition can be adjusted, if necessary, with suitable acid, base, or buffer. Suitable bulking, dispersing, wetting or suspending agents, including mannitol and polyethylene glycol (such as PEG 400), can also be included in the composition. A suitable parenteral composition can also include a compound of the present invention lyophilized in injection vials. Aqueous solutions can be added to dissolve the composition prior to injection.

The pharmaceutical compositions can be administered in the form of a suppository or the like. Such rectal formulations preferably contain the compound of the present invention in a total amount of, for example, about 0.075 to about 75% w/w, or about 0.2 to about 40% w/w, or about 0.4 to about 15% w/w. Carrier materials such as cocoa butter, theobroma oil, and other oil and polyethylene glycol suppository bases can be used in such compositions. Other carrier materials such as coatings (for example, hydroxypropyl methylcellulose film coating) and disintegrants (for example, croscarmellose sodium and cross-linked povidone) can also be employed if desired.

These pharmaceutical compositions can be prepared by any suitable method of pharmaceutics, which includes the step of bringing into association the compound of the present invention and a carrier material or carrier materials. In general, the compositions are uniformly and intimately admixing the compound with a liquid or finely divided solid carrier, or both, and then, if necessary, shaping the product. For example, a tablet can be prepared by compressing or molding a powder or granules of the compound, optionally with one or more accessory ingredients. Compressed tablets can be prepared by compressing, in a suitable machine, the compound in a free-flowing form, such as a powder or granules optionally mixed with a binding agent, lubricant, inert diluent and/or surface active/dispersing agent(s). Molded tablets can be made by molding, in a suitable machine, the powdered compound moistened with an inert liquid diluent.

Tablets of the present invention can also be coated with a conventional coating material such as Opadry™ White YS-1-18027A (or another color) and the weight fraction of the coating can be about 3% of the total weight of the coated tablet. The pharmaceutical compositions of the present invention can be formulated so as to provide quick, sustained or delayed release of the compound of the present invention after administration to the patient by employing procedures known in the art.

When the excipient serves as a diluent, it can be a solid, semi-solid or liquid material, which acts as a vehicle, carrier or medium for the compound of the present invention. Thus, the compositions can be in the form of tablets, chewable tablets, pills, powders, lozenges, sachets, cachets, elixirs, suspensions, emulsions, solutions, syrups, aerosols (as a solid or in a liquid medium), soft and hard gelatin capsules and sterile packaged powders.

In one embodiment of the present invention, the manufacturing processes may employ one or a combination of methods including: (1) dry mixing, (2) direct compression, (3) milling, (4) dry or non-aqueous granulation, (5) wet granulation, or (6) fusion. Lachman et al., *The Theory and Practice of Industrial Pharmacy* (1986).

In another embodiment, solid compositions, such as tablets, are prepared by mixing a compound of the present invention with a pharmaceutical excipient to form a solid preformulation composition containing a homogeneous mixture of the compound of the present invention and the excipient. When referring to these preformulation compositions(s) as homogeneous, it is meant that the compound is dispersed evenly throughout the composition so that the composition may be readily subdivided into equally effective unit dosage forms, such as tablets, pills and capsules. This solid preformulation is then subdivided into unit dosage forms of the type described herein.

Compressed tablets are solid dosage forms prepared by compacting a formulation containing a compound of the present invention and excipients selected to aid the processing and improve the properties of the product. The term "compressed tablet" generally refers to a plain, uncoated tablet for oral ingestion, prepared by a single compression or by pre-compaction tapping followed by a final compression.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. A variety of materials can be used for such enteric layers or coatings, including a number of polymeric acids and mixtures of polymeric acids with such materials as shellac, cetyl alcohol and cellulose acetate.

Use of a long-term sustained release implant may be suitable for treatment of cancer in patients who need continuous administration of the compositions of the present invention. "Long-term" release, as used herein, means that the implant is constructed and arranged to deliver therapeutic levels of the compound of the present invention for at least 30 days, and preferably 60 days. Long-term sustained release implants are well known to those of ordinary skill in the art and include some of the release systems described above.

The invention will be further described by reference to the following detailed Examples. The following Examples are intended to illustrate various aspects of the invention and should not be construed as to narrow its scope. One skilled in the art will readily recognize that the Examples suggest many other ways in which the present invention could be practiced. It should be understood that many variations and modifications may be made while remaining within the scope of the invention.

EXAMPLES

Example 1

Syntheses of Phosphoramidates

A. Synthesis of Methyl chlorophenylphosphoryl P→N-Alaninate

Methyl chlorophenylphosphoryl P→N-Alaninate was synthesized using the procedure described in the literature (Qiu et al., 1999). Briefly, to a suspension of methyl L-alaninate hydrochloride (1.40 g, 10 mmol) and phenyl dichlorophosphate (1.56 mL, 10 mmol) in $CH_2Cl_2$ (80 mL) at −80° C., a solution of triethylamine (2.79 mL, 20 mmol) in $CH_2Cl_2$ (60 mL) was added dropwise over 2 hours with continuous stirring. The solvent was evaporated and 30 mL of ether was added to the residue. The insoluble portion was filtered off and washed twice with 5 mL volumes of ether. The solvent was evaporated and the colorless oil was used as 0.184 M or 50 mg/mL stock solution in dry tetrahydrofuran. Yields for the reaction varied between 90-95%.

B. Synthesis of Methyl Thymidine-5'-phenylphosphoryl-P→N-alaninate

Methyl thymidine-5'-phenylphosphoryl-P→N-alaninate was synthesized using a modified procedure described in the literature (Winter et al., 1996). Thymidine (242.2 mg, 1 mmol) in dry THF (12 mL) was sonicated for 5 minutes and a solution of methyl chlorophenylphosphoryl P→N alaninate (12 mL of 0.184 M solution in THF) was added. After the addition of N-Methyl imidazole (0.34 mL, 4.2 mmol), the reaction mixture was stirred at room temperature for 3 hours. The solvent was evaporated, and the residue was dissolved in the minimum amount of $CH_2Cl_2$. The crude product was purified using chromatography on a silica gel column using $CH_2Cl_2$:MeOH (96:4) solvent system, to yield a colorless amorphous solid (300 mg, 62.1%), a mixture of two diastereoisomers. HPLC demonstrated a single peak with a retention time of 11.7 minutes on a semi prep Econosil C-18 column (10μ, 250×4.6 mm). Compound purity was greater than 99%.

Spectral Analysis:

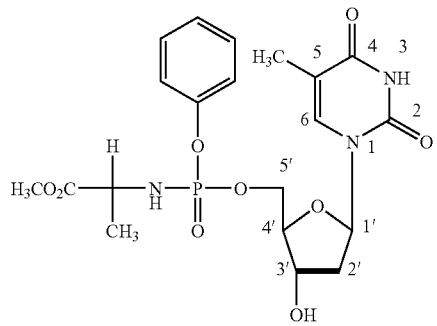

$^1$H NMR ($CD_3SOCD_3$) δ 1.20 (apparent t, 3H, $CH_3$ of Ala), 1.80 (poorly resolved d, 3H, 5-$CH_3$), 2.04 (m, 2H, $H_{2'}$), 3.56 (s, 3H, $OCH_3$), 3.83 (m), 3.94 (apparent d) and 4.07-4.26 (m, total 5H, $H_{3'}$, $H_{4'}$, $H_{5'}$, CHN of Ala), 5.40 and 5.41 (2 d, J=4.0 Hz, 3'-OH), 6.08 (t, NH of Ala) and 6.18 (m, $H_{1'}$, total 2H), 7.17 and 7.34 (2 m, 5H, $C_6H_5$), 7.46, 7.48 (2d, 1H, $H_6$), 11.31 (s, 1H, 3-NH).

$^{13}$C NMR ($CD_3SOCD_3$) ppm 12.63, 12.69 (5-$CH_3$), 20.88, 20.93 ($CH_3$ of Ala), 40.00, 40.12 ($C_{2'}$), 50.37, 50.51 (CHN, Ala), 52.81, 52.85 ($CH_3O$), 66.26, 66.57 ($C_{5'}$), 70.87, 71.12 ($C_{3'}$), 84.89, 85.00, 85.17, 85.27 (overlapped $C_{1'}$ and $C_{4'}$), 111.44 ($C_5$), 120.23, 120.33 (meta-C, $C_6H_5$), 125.41, 125.46 (ortho-C, $C_6H_5$), 130.00 (para-C, $C_6H_5$), 135.85, 135.97 ($C_6$), 150.58, 150.65, 150.97 (ipso-C, $C_6H_5$ and $C_2$), 164.50 ($C_4$), 174.34, 174.41 (C=O, Ala).

$^{31}$P NMR ($CD_3SOCD_3+D_2O$) ppm 4.85 and 5.03.

Electrospray ionization (ESI)-MS (MeOH+NaCl) m/e 506 (100.0, M+Na), 989 (30.2, 2M+Na).

Anal. Calcd for $C_{20}H_{26}N_3O_9P\times0.5\ H_2O$: C, 48.78; H, 5.53; N, 8.53. Found: C, 48.58; H, 5.47; N, 8.48.

C. Synthesis of (1-(2'-deoxy-2'-fluoro-β-D-arabinofuranosyl)-uracil-5'-(phenyl methoxyalaninyl phosphate (FAU-PA)))

FAU (247.1 mg, 0.834 mmol) in dry THF (8 mL) was sonicated for 5 minutes. After the addition of N-methyl imidazole (0.5 mL, 6.2 mmol), a solution of methyl chlorophenylphosphoryl P→N alaninate (30 mL, 0.18 4M solution in THF) was added continuously over a period of 4 hours with continuous stirring. The reaction was monitored on a HPLC system using Econosil C-18 column (10μ, 250×10 mm) with 30% acetonitrile as the mobile phase at 5 mL/minute. When the product concentration could not be improved, solvent was evaporated and the crude reaction mixture was purified using the above-mentioned column by semi-prep HPLC. Retention time for the pure diastereoisomeric mixture was 16.9 and 17.6 minutes (flow rate of 2.5 mL/minute). The product fractions were collected; water and acetonitrile were evaporated under reduced pressure. Freeze drying of the mixture on a lyophilizer resulted in a white amorphous solid (254 mg, 62.5%).

Spectral Analysis: UV spectrum (EtOH) $\lambda_{max}$ 260 nm (ε 13,300), 204 nm (ε 21,000).

$^1$H NMR ($CD_3SOCD_3$) δ 1.21 (apparent t, 3H, $CH_3$ of Ala) 3.566 and 3.572 (2 s, 3H, $CH_3O$), 3.84 (m, 1H), 3.98-4.05 (m, 1H) and 4.10-4.26 (2 m, 3H, $H_{3'}$, $H_{4'}$, $H_{5'}$, CHN of Ala), 5.04

(dm, $J_{2',F}$=52.8 Hz, $H_{2'}$), 5.55 and 5.56 (d, J=8.0 Hz, $H_5$), 6.05-6.18 (m, 3H, $H_{1'}$, OH, NH of Ala), 7.18 and 7.35 (2 m, 5H, $C_6H_5$), 7.55 and 7.57 (2 overlapped d, $H_6$), 11.49 (s, 1H, NH of Ura).

$^{13}$C NMR ($CD_3SOCD_3$) ppm 20.31 ($CH_3$), 50.33, 50.46 (CHN of Ala), 52.57 ($CH_3O$), 65.53 ($C_{5'}$), 73.70, 73.94 ($C_{3'}$), 82.05, 83.55, 83.71 ($C_{1'}$, $C_{4'}$), 95.68 (d, J=191.1 Hz, $C_{2'}$), 101.92 ($C_5$), 120.78, 120.83 (meta-C, $C_6H_5$), 125.30 (ortho-C, $C_6H_5$), 130.31, 130.34 (para-C, $C_6H_5$), 141.77 ($C_6$), 150.79, 151.18, 151.32 (ipso-C, $C_6H_5$ and $C_2$), 163.60 ($C_4$), 174.22, 174.34 (C=O, Ala).

$^{19}$F NMR ($CD_3SOCD_3$) ppm 199.04 (m).

$^{31}$P NMR ($CD_3SOCD_3$) ppm 4.86 and 4.87.

EI-MS (MeOH+NaCl) m/e 85 (100.0), 488 (14.1, M+H), 510 (18.2, M+Na), 997 (3.5, 2M+Na).

Anal. Calcd for $C_{19}H_{23}FN_3O_9P$: C, 46.82; H, 4.76; N, 8.62. Found: C, 47.06; H, 4.96; N, 8.65.

D. Cell Lines

Renca, a mouse renal carcinoma cell line used for these studies, was a gift from Dr. G. Gali Hillman, Wayne State University. Cells were cultured in RPMI-1640 medium containing L-glutamine (Gibco) supplemented with 10% (v/v) fetal bovine serum (FBS), 100 U/mL penicillin, and 0.1 mg/mL streptomycin. Cells were cultured at 37° C. in a humidified incubator with a gas phase of 95% air and 5% $CO_2$.

E. Tracer Uptake Studies

Tracer uptake studies were performed using [H-3]FAU (318.2 GBq/mmol, >99% radiochemical purity), and [H-3] FAU-PA (9.25 GBq/mmol, >99% radiochemical purity). Radiochemicals were obtained from Moravek Biochemicals (Brea, Calif.).

Renca cells were seeded at $2\times10^5$ cells/mL in 6 well plates. After 48 hours, when cells were 50-60% confluent, culture medium was replaced with 1 mL medium containing either 1 µCi/mL of [H-3]FAU or [H-3]FAU-PA. Cells were incubated in a humidified incubator for two hours at 37° C. in an atmosphere of 5% $CO_2$ and 95% air. At the end of the incubation period, radioactive medium was removed, and cells were rinsed three times with ice cold phosphate buffered saline (PBS). Then, cells were trypsinized, centrifuged at 2000 g for 5 minutes and rewashed three times with ice cold PBS. The cell pellet was dissolved using 0.2 mL of soluene-350 solution. All the supernatants and pellet samples were mixed with 5 mL of Ultima Gold scintillation cocktail and counted for 5 minutes in a liquid scintillation counter. Activity in the final wash was used as background and was deducted from the pellet activity. Experiments were done in triplicate and an external standard quench correction was used during beta isotope counting.

F. DNA Incorporation Studies

Two days after seeding $1\times10^6$ cells in 100×20 mm culture dishes, culture medium was replaced with 1 mL medium containing either 1 µCi/mL of [H-3] FAU or [H-3] FAU-PA. Cells were incubated in a humidified incubator for two hours at 37° C. in an atmosphere of 5% $CO_2$ and 95% air. At the end of the incubation period, radioactive medium was removed and cells were washed three times with ice cold PBS. Then, cells were trypsinized, centrifuged and rewashed three times with ice cold PBS. Cells were lysed with 1 mL of 1M ice-cold perchloric acid solution. The cell lysates were vortexed and centrifuged at 14000 g for 15 minutes. The supernatants were removed, and the pellets were rinsed twice with 1 mL PCA. The acid insoluble fractions were resuspended in 200 µl of Soluene-350. All the acid soluble fractions or supernatants and the acid insoluble fractions were mixed with 5 mL of Ultima Gold scintillation cocktail and counted for 5 minutes on a liquid scintillation counter after an overnight chilling. Experiments were done in triplicate, and external standard quench correction was used during beta isotope counting.

G. Pig Liver Esterase Studies

Thymidine and phosphoramidate analogs were dissolved in 0.02 M $Na_2HPO_4$ at a concentration of 1 mg/mL and 200 units of pig liver esterase per mL solutions (Sigma, St. Louis, Mo.) were added. The mixtures were stirred and maintained at 37° C. through out the course of the experiment. The rate of hydrolysis was followed by thin layer chromatography (TLC) from reaction mixture samples collected at selected intervals. For TLC monitoring, $CH_2Cl_2$:MeOH (4:1) and i-PrOH: $NH_4OH$:$H_2O$ (7:1:2) mobile phases were used. At the completion of hydrolysis, within 30 minutes, samples were run on a HPLC system.

Example 2

Growth Inhibition Studies with Unlabeled FAU and FAU-PA

A. Cell Lines

The cell lines CEM (T lymphoblastoid cells derived from a human peripheral blood), MOLT-4 (derived from a human acute lymphoblasticleukemia), RAJI (derived from a human Burkitt lymphoma), U-937 (derived from a human histocytic lymphoma), and K-562 (derived from a human chronic myelogenous leukemia) were used to measure the cytotoxicity, as assessed by growth inhibition potential. The cell lines were purchased from the American Type Culture Collection (Vienna, Va.). The cells were grown and maintained as a suspension culture in a RPMI 1640 preparation containing L-glutamine (Biofluids, Rockville, Md.) and 10% (v/v) heat-inactivated fetal calf serum (Invitrogen, Chicago, Ill.); a penicillin-streptomycin solution (Sigma Chemical Co., St. Louis, Mo.) was added to achieve a final concentration of 100 units/ mL, and 100 µg/mL respectively. Cells were maintained at 37° C. in a humidified 5% $CO_2$ atmosphere and were passed every 72-96 h to maintain cell densities of approximately 30,000 to 40,000 cells/mL. Under these conditions, the doubling times for CEM cells, MOLT-4 cells, RAJI cells, U-937 cells, and K-562 cells were 21-22 hours.

B. Preparation of Drug

FAU and FAUPA were dissolved in deionized water and sterilized by passing through a Millex-GV, 0.22 µm filter, Millipore, Bedford, Mass.

C. Toxicity Studies

All cell lines were resuspended in fresh media at 3000 to 3500 cells/mL. To each cell suspension final volume 0.2 mL, was added to achieve 0 to 1000 µM concentration of either FAU or FAU-PA. Control experiments had appropriate amounts of sterile distilled water instead of the drug. Incubation was conducted at 37° C. in a humidified 5% $CO_2$ and 95% air atmosphere for 72 hours, and the inhibition of cellular growth was assessed by cell counting on Beckman Coulter Z2 Particle Count and Size Analyzer (Miami, Fla.).

RESULTS

Phosphoramidate syntheses: Both thymidine and FAU 5' phosphoramidates were synthesized in more than 60% yield. Both the compounds were diasteroisomers with >99% chemical purity. The diastereoisomers were not separated. Spectral analysis of the compounds was described in the methods section.

Tracer uptake and incorporation studies: Incubation of Renca cells for two hours with [H-3]FAU and [H-3]FAU-PA resulted in more than a 17 fold higher intracellular accumulation of activity with FAU-PA. The PCA extraction analysis showed at least a 17 and 10-fold increase activity in acid soluble and insoluble fractions with FAU-PA, respectively. Out of the total accumulated activity, 80% of activity with FAU and 72% in the case of FAU-PA were found in the acid insoluble fraction (FIGS. 2 and 3).

Figure 2:
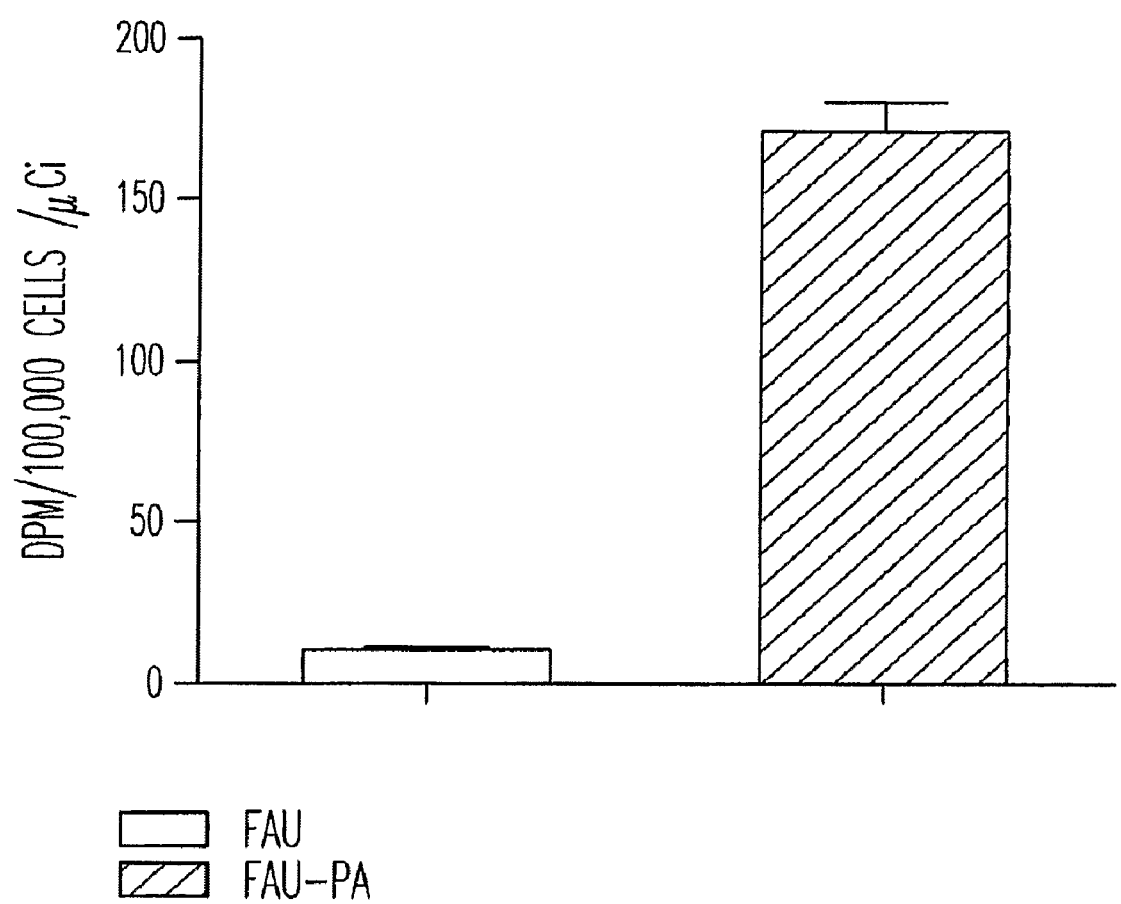
FIGS. 2 and 3: Intracellular accumulation of FAU and FAU-PA.
Figure 3:
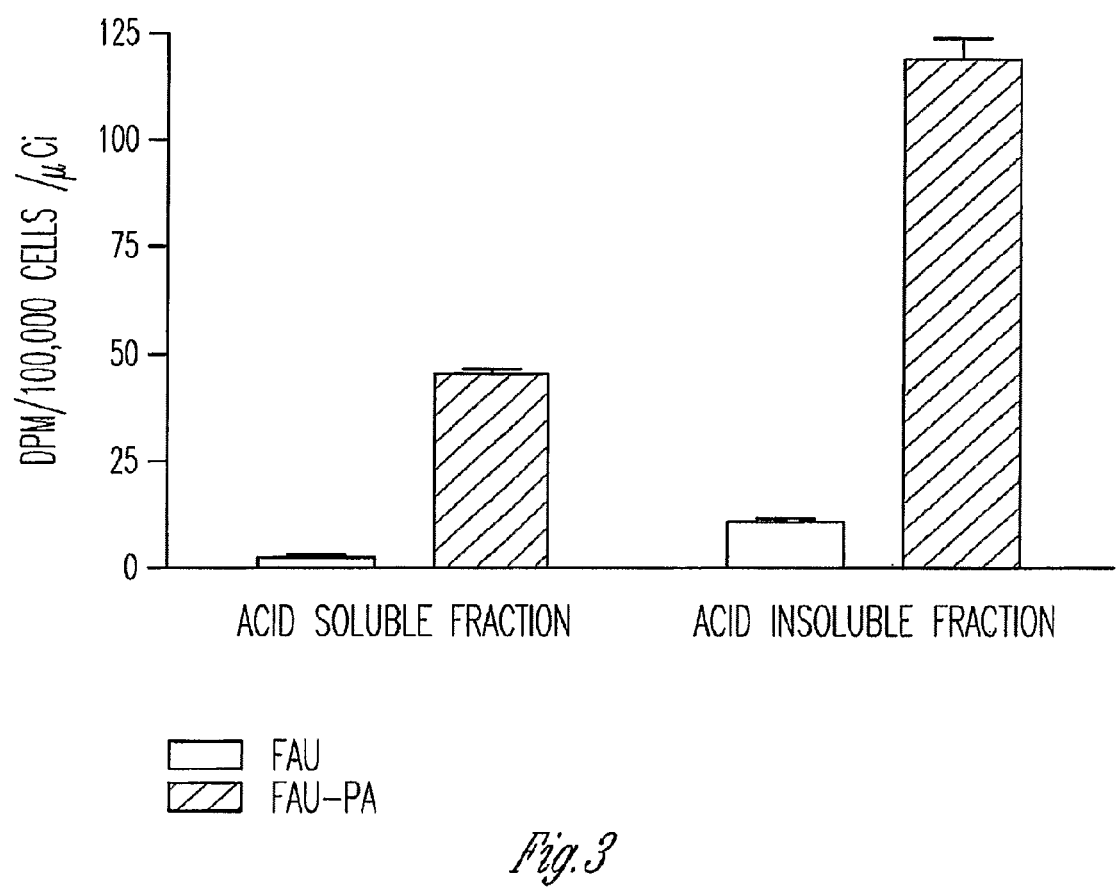

FIG. 2 represents the intracellular accumulation of FAU-PA and FAU. FIG. 3 shows the acid extraction analysis results. FAU-PA shows 17 times higher total accumulation than FAU. Also, the acid soluble and acid insoluble fractions from FAU-PA incubated cells contained 18 and 11 times higher activity than their counterparts from FAU incubated cells, respectively.

Enzymatic hydrolysis: Incubation of thymidine and FAU phosphoramidates with pig liver esterase resulted in a polar metabolite with both compounds. The rate of hydrolysis was faster for FAU-PA (within 15 minutes) compared to thymidine-PA (15-30 minutes). The retention times for the thymidine-PA and FAU-PA metabolites were 3.5 minutes.

Figure 4:
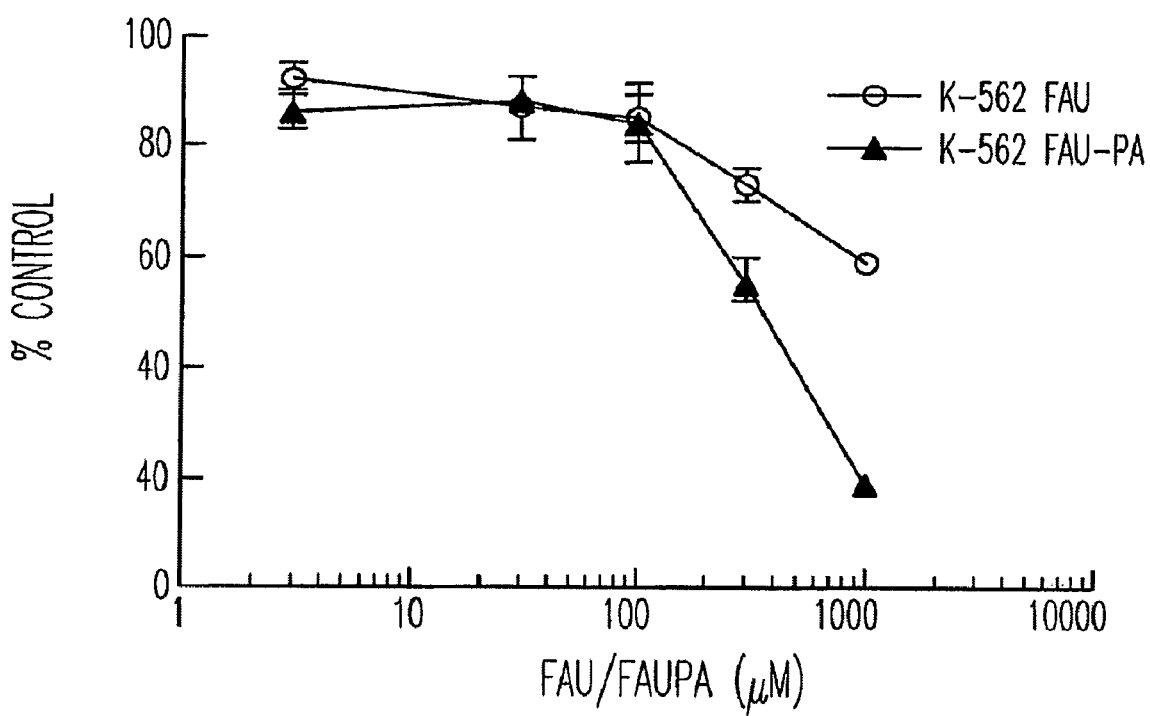
FIG. 4: Growth inhibition studies with FAU-PA and FAU. Cells were seeded at 3000-3500 cells/well and incubated for 72 hours with FAU or FAU-PA. Final concentration of the drugs varied from 3-1000 μM. Cell growth inhibition was presented as a percentage of control.
Figure 5:
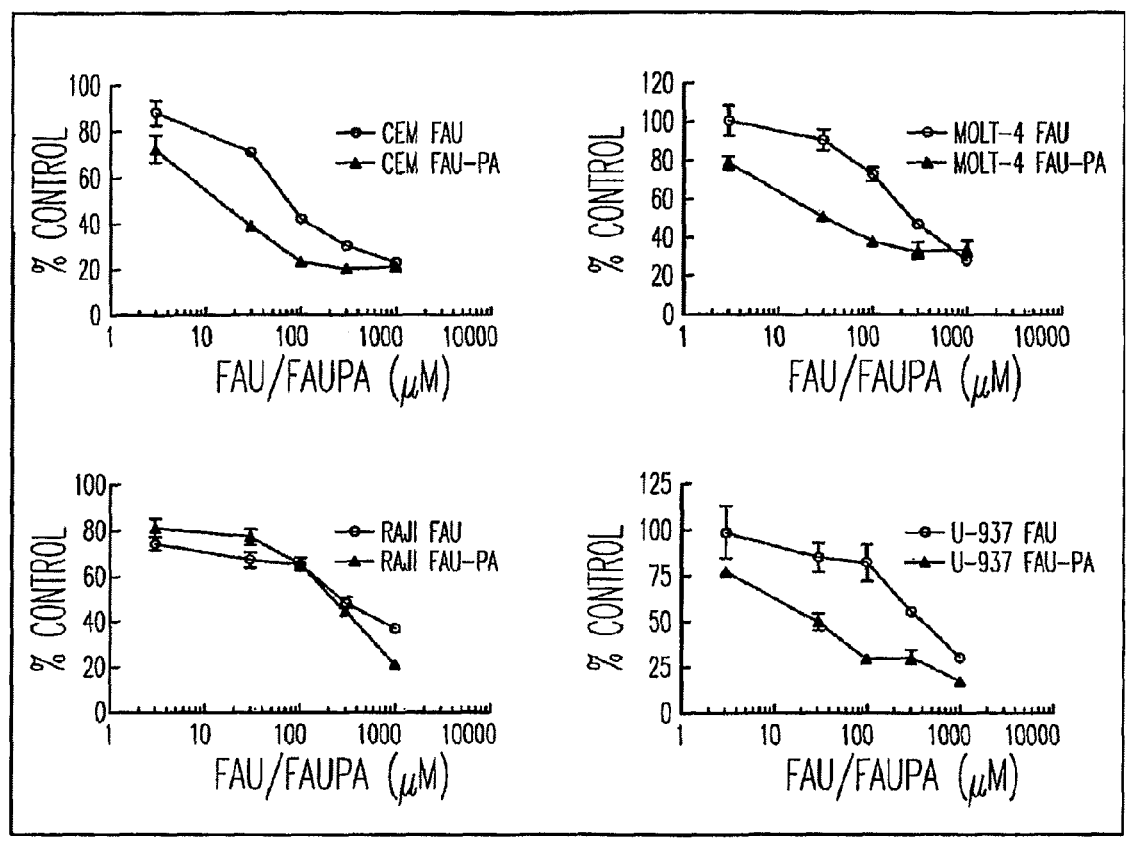
FIG. 5: Cells were seeded at 3000-3500 cells/well and incubated for 72 hours with FAU or FAU-PA. Final concentration of the drugs varied from 3 to 1000 μM. Cell growth inhibition was presented as a percentage of control.

Growth inhibition studies: Cell lines used for growth inhibition studies were chosen based on a range of DNA incorporation values for FAU. Cells were seeded at 3000-3500 cells/well and incubated for 72 hours with FAU or FAU-PA. Final concentration of the drugs varied from 3-1000 µM. After the incubation period cell growth inhibition was presented as a percentage of control. Continuous incubation with FAU and FAU-PA produced various degrees of growth inhibition. Inhibition rates were higher for FAU-PA treated cells (FIGS. 4 and 5). In the case of FAU-PA, the $IC_{50}$ values were less than 60 µM for MOLT, CEM and U-937 and greater than 100 µM for Raji and K-567 cells. With FAU, only CEM cells showed an $IC_{50}$ less than 100 µM. MOLT, U-937, Raji were somewhat less inhibited at 1 mM, and K-562 was only 40% inhibited even at 1 mM concentration.

Phosphoramidate analogs of various nucleosides, including that of FLT (Drontle and Wagner, 2004), d4T and AZT (Saboulard et al., 1999), have been synthesized to improve efficacy of the compounds as antiviral compounds. Some of these attempts were met with limited success, but none have reached the pharmacy. The synthesis of 5'-phosphoramidates of thymidine and FAU can be accomplished in reasonable yields. Thymidine has been used mostly as a model system to determine the reaction conditions. FAU was hypothesized to be sequentially activated by thymidine kinase and thymidylate synthase, converted into FMAU-monophosphate before incorporated into DNA.

Many drugs have been developed (e.g. 5FU) with the goal of inhibiting TS in tumors. While some of these strategies have been very successful, tumors have developed resistance to these drugs over time. One of the reasons for this resistance is an increased expression level of TS. FAU was developed as a prodrug to utilize the high expression levels of TS in these tumors. Consistent with this hypothesis, FAU showed higher toxicity in cell lines with high TS expression levels (Collins et al., 1999). FAU was also found to be a poor substrate for mammalian cytosolic thymidine kinase (TK1) (Sun et al., 2003). The present phosphoramidate analogs can deliver the FAU-phosphate intracellularly, eliminating the need for phosphorylation of FAU in the cell.

Initial studies using the [H-3]FAU-PA showed a considerable (17 fold) increase in accumulation of activity in Renca cells over [H-3]FAU. This could have been possible merely due to the high lipophilicity of the molecule. Further analysis with PCA extraction studies found 72% of the accumulated activity in the acid insoluble fraction. This is a considerable fraction to be incorporated into DNA in a two hour time period.

Growth inhibition studies using unlabeled FAU-PA in cell lines with varying TS levels produced different levels of inhibition with better toxicity profile than FAU. CEM, with the highest expression of TS in the panel of chosen cell lines, showed higher growth inhibition with both FAU and FAU-PA. MOLT and U-937 cell lines, with lower TS activity than CEM, showed similar inhibition profile that of CEM in case of FAU-PA. Raji and K-562 cells showed little growth inhibition with both the drugs. In the literature, it has been reported that K-562 cells incubated with FAU have high levels intracellular FAU-monophosphate (Collins et al., 1999). The reason for this poor toxicity is unknown. Studies with phosphoramidates of other analogs such as d4T and AZT have shown toxicity due to the formation of amino acyl metabolites, which are formed as an intermediate in the phosphoramidate to phosphate conversion process (Saboulard et al., 1999).

LITERATURE CITED

T. W. Abraham et al. (1996) *J Med Chem* 39:4569-4575.
G. Antonelli et al. (1996) *AIDS Res Hum Retroviruses* 12:223-228.
J. Balzarini et al. (1996) *Proc Natl Acad Sci USA* 93:7295-7299.
J. Balzarini et al. (1997) *FEBS Lett* 410:324-328.
Y. C. Cheng et al. (1983) *J Biol Chem* 258:12460-12464.
J. M. Collins et al. (1999) *Clin Cancer Res* 5:1976-1981.
K. W. Culver et al. (1992) *Science* 256:1550-1552.
D. P. Drontle et al. (2004)*Mini Rev Med Chem* 4:409-419.
S. M. Dudkin et al. (1971) *FEBS Lett* 16:48-50.
J. L. Eiseman et al. (2004) *Clin Cancer Res* 10:6669-6676.
S. N. Farrow et al. (1990) *J Med Chem* 33:1400-1406.
H. N. Fernley (1971) in *The Enzymes*; pp. 417-447, Academic Press, New York.
A. K. Field et al. (1983) *Proc Natl Acad Sci USA* 80:4139-4143.
M. E. Holzer et al. (1962)*Biochim Biophys Acta* 56:491-501.
M. E. Holzer et al. (1966) *Biochim Biophys Acta* 122:232-243.
M. Inaba et al. (1998) *Biol Pharm Bull* 21:569-573.
M. Johansson (1999) *J Biol Chem* 274:23814-23819.
S. J. Kelly et al. (1975) *Biochemistry* 14:4983-4988.
R. W. Klecker et al. (1994) *Mol Parmacol* 46:1204-1209.
W. Knecht et al. (2000) *J Mol Biol* 301:827-837.
M. Kuba et al. (1994) *Int J Biochem* 26:235-245.
C. McGuigan et al. (1998a) *Antivir Chem Chemother* 9:473-479.
C. McGuigan et al. (1998b) *Antivir Chem Chemother* 9:109-115.
E. J. McIntee et al. (1997) *J Med Chem* 40:3323-3331.
F. L. Moolten (1986) *Cancer Res* 46:5276-5281.
F. L. Moolten et al. (1990) *J Natl Cancer Inst* 82:297-300.

F. L. Moolten et al. (1990) *Hum Gene Ther* 1:125-134.
B. Munch-Petersen et al. (2000) *J Biol Chem* 275:6673-6679.
B. Munch-Petersen et al. (1998) *Adv Exp Med Biol* 431:465-469.
M. Nishino et al. (1994) *Arch Biochem Biophys* 312:101-106.
R. Parvin et al. (1969) *Biochemistry* 8:1748-1755.
Y. L. Qiu et al. (1999) *Antiviral Res* 43:37-53.
D. Saboulard et al. (1999) *Mol Pharmacol* 56:693-704.
Z. A. Shabarova et al. (1970) *FEBS Lett* 11:237-240.
M. F. Singer et al. (1957) *J Biol Chem* 229:111-119.
S. L. Snyder et al. (1972) *Biochemistry* 11:3220-3223.
J. R. Stevens-Clark et al. (1968a) *J Biol Chem* 243:4474-4478.
J. R. Stevens-Clark et al. (1968b) *J Biol Chem* 243:4468-4473.
H. Sun et al. (2003) *Nucl Med Biol* 30:25-30.
O. Turriziani et al. (1996) *Biochem Biophys Res Commun* 228:797-801.
G. Valette et al. (1996) *J Med Chem* 39:1981-1990.
H. Wang et al. (2002) *Cancer Chemother Pharmacol* 49:419-424.
H. Winter et al. (1996) *J Med Chem* 39:3300-3306.
S. Wu et al. (1995) *J Acquir Immune Defic Syndr Hum Retrovirol* 8:1-9.
J. Zemlicka (2002) *Biochim Biophys Acta* 1587:276-286.

All cited publications, patents and patent applications are incorporated herein by reference. While in the foregoing specification this invention has been described in relation to certain preferred embodiments, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A compound of formula I:

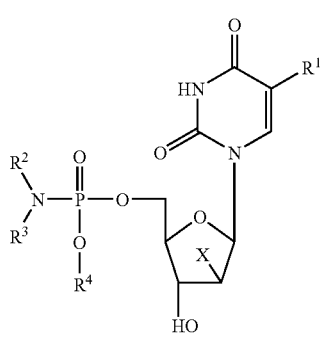

(I)

wherein
$R^1$ is H, F, or $(C_1-C_4)$alkyl;
X is F;
$R^4$ is phenyl, optionally substituted with 1-3 nitro, 1-5 halo, 1-3 $(C_1-C_6)$alkyl, 1-2 $CF_3$ groups, or a combination thereof;
$R^2$ and $R^3$ are individually H or $(C_1-C_6)$alkyl optionally substituted with 1 or 2 hydroxy, $(C_1-C_6)$alkoxy, $(C_1-C_6)$alkylthio, phenyl, $(C_6-C_{12})$aryloxy, cyano, $(C_1-C_6)$alkoxycarbonyl, amido, $(C_1-C_6)$alkyl-amido, $(C_1-C_6)$alkylsulfonyl, $(C_6-C_{12})$arylsulfonyl, $(C_1-C_6)$perfluoroalkyl-sulfonyl, $(C_1-C_6)$alkylsulfinyl, and $(C_6-C_{12})$arylsulfinyl, or $R^2$ and $R^3$ taken together with N are a 5- or 6-membered heteroaryl or heterocyclic ring optionally containing 1 or 2 additional S, N, or O atoms, wherein N is substituted with $R^5$, and $R^5$ is H, O, $(C_1-C_4)$alkyl, phenyl, or benzyl;
with the proviso that one of $R^2$ and $R^3$ is not H;
or a pharmaceutically acceptable salt thereof.

2. A compound of claim 1 wherein $R^1$ is H.
3. The compound of claim 1 wherein $R^4$ is phenyl.
4. The compound of claim 1 wherein $R^2$ is H.
5. The compound of claim 1 wherein $R^3$ is phenyl$(C_1-C_4)$alkyl.
6. The compound of claim 1 wherein $R^3$ is $(C_1-C_4)$alkoxycarbonyl-$(C_1-C_6)$alkyl.
7. The compound of claim 1 wherein $R^3$ is 1-$((C_1-C_4)$alkoxy-carbonyl)ethyl-.
8. The compound of claim 1 wherein $R^3$ is 1-(methoxycarbonyl)ethyl-.
9. The compound of claim 1 wherein F is $^{18}$F.
10. A pharmaceutical composition comprising a compound of claim 1 and a pharmaceutically acceptable diluent or carrier.
11. A method of inhibiting the growth of cancer cells comprising contacting said cells with an effective growth inhibiting amount of a compound of claim 1.
12. The method of claim 11 wherein the inhibition is accomplished by administering the compound to a mammal afflicted with cancer.
13. The method of claim 12 wherein the cancer is susceptible to 5-FU.
14. The method of claim 11 wherein the cancer is breast, colorectal, head or neck cancer.
15. The method of claim 12 wherein the mammal is a human.
16. The method of claim 11 wherein the compound is administered parenterally.
17. The method of claim 11 wherein the compound is administered orally.
18. A method of imaging a tumor comprising administering to a mammal afflicted with a tumor, an effective imaging amount of a compound of claim 1 and employing the techniques of positron emission tomography (PET) to produce images of said tumor.

* * * * *